US008875580B2

(12) United States Patent  
Yost et al.

(10) Patent No.: US 8,875,580 B2  
(45) Date of Patent: Nov. 4, 2014

(54) METHOD AND APPARATUS TO DETECT WIRE PATHOLOGIES NEAR CRIMPED CONNECTOR

(75) Inventors: William T. Yost, Newport News, VA (US); Karl Elliott Cramer, Yorktown, VA (US); Daniel F. Perey, Yorktown, VA (US)

(73) Assignee: The United States of America as represented by the Adminstrator of the National Aeronautics and Space Adminstration, Washington, DC (US)

( * ) Notice: Subject to any disclaimer, the term of this patent is extended or adjusted under 35 U.S.C. 154(b) by 368 days.

(21) Appl. No.: 13/324,527

(22) Filed: Dec. 13, 2011

(65) Prior Publication Data  
US 2013/0145849 A1 Jun. 13, 2013

(51) Int. Cl.  
*G01N 29/07* (2006.01)

(52) U.S. Cl.  
USPC .............................................. 73/598; 73/602

(58) Field of Classification Search  
USPC ..................... 73/598, 600, 602, 620, 624  
See application file for complete search history.

(56) References Cited

U.S. PATENT DOCUMENTS

| | | | |
|---|---|---|---|
| 3,157,075 A | 11/1964 | Filia et al. | |
| 3,292,413 A | 12/1966 | Falcioni | |
| 4,062,227 A | 12/1977 | Heyman | |
| 4,385,515 A | 5/1983 | Link et al. | |
| 5,046,241 A | 9/1991 | Ricard | |
| 5,092,026 A | 3/1992 | Klemmer et al. | |
| 5,297,435 A | 3/1994 | Papazian | |
| 5,314,105 A * | 5/1994 | Farassat | 228/102 |
| 5,767,408 A * | 6/1998 | Lindgren et al. | 73/597 |
| 5,814,728 A | 9/1998 | Okawa et al. | |
| 5,894,092 A * | 4/1999 | Lindgren et al. | 73/598 |
| 6,076,411 A * | 6/2000 | Horvath | 73/866 |
| 6,196,062 B1 | 3/2001 | Wright et al. | |
| 6,393,924 B1 | 5/2002 | Eder et al. | |
| 6,418,769 B1 | 7/2002 | Schreiner | |
| 6,553,803 B1 | 4/2003 | Heingartner et al. | |
| 6,745,629 B2 * | 6/2004 | Farassat | 73/582 |
| 7,181,942 B2 | 2/2007 | Yost et al. | |
| 8,490,463 B2 * | 7/2013 | Yost et al. | 73/1.82 |
| 2012/0192407 A1* | 8/2012 | Yost et al. | 29/593 |
| 2013/0197823 A1* | 8/2013 | Williams | 702/39 |

* cited by examiner

*Primary Examiner* — J M Saint Surin  
(74) *Attorney, Agent, or Firm* — Andrea Z. Warmbier

(57) ABSTRACT

A method and apparatus for evaluating and/or quantifying damage to wire strands of a wire caused during installation of a crimped wire connector, involves launching an ultrasonic wave having known characteristics into a wire at a location that is either the crimp or is adjacent the crimped wire connector, and detecting changes in the characteristics (e.g., amplitude and/or phase shift) of the wave as it is propagates along a length of the wire.

16 Claims, 3 Drawing Sheets

METHOD AND APPARATUS TO DETECT WIRE PATHOLOGIES NEAR CRIMPED CONNECTOR

STATEMENT REGARDING FEDERALLY SPONSORED RESEARCH OR DEVELOPMENT

The invention described herein was made by employees of the United States Government and may be manufactured and used by or for the Government of the United States of America for governmental purposes without the payment of any royalties thereon or therefor.

FIELD OF THE INVENTION

This invention relates to the use of ultrasonic technology to evaluate the integrity of a wire in the immediate vicinity of a crimp connection.

BACKGROUND OF THE INVENTION

Electrically conductive stranded wires are frequently terminated with a crimped connection as an alternative to electrical connectors made using soldering, welding, conductive adhesives, and various types of solderless techniques such as insulation displacement, compression, wire clamping and interference fit connections. Crimp connectors are often preferred because they are reliable, inexpensive, easily replaced if damaged, and can provide uniform and reproducible electrical and mechanical characteristics. However, damage to the electrically conductive wires can occur in the immediate vicinity of a crimped connection. This can cause a failure mode that significantly shortens the service life of a crimp connection leading to a failure of a system or vehicle employing the connection. Consequently, it is desirable to reliably and inexpensively evaluate the integrity of a crimped connector.

It is conceivable that an electrical resistance test through a crimped connector may be used to validate or evaluate the connection. However, such testing is not normally done in a production environment due to the high cost and impracticality of such testing and the inability to accurately predict failures due to certain latent damages such as small nicks or indentations that could be difficult or nearly impossible to detect by resistance testing, but which can create mechanical weaknesses that can propagate and eventually lead to an electrical failure.

Another commonly employed technique for determining the damage caused during fabrication of a crimped connector is visual inspection. Unfortunately, visual inspection is not easily employed for small wire diameters or when the crimp connection is not easily accessible, such as when the crimp connector is under a ferrule apron or at a junction between a wire and its insulation.

BRIEF SUMMARY OF THE INVENTION

In certain embodiments, an ultrasonic wave is propagated from a source along a length of an electrically conductive wire in the vicinity of a crimp connection. At a predetermined distance from the source, the wave is detected and compared with the propagated ultrasonic wave. Based on comparisons, including wave energy and phase shifts, the existence and extent of damage to the wire in the vicinity of the crimp connection is evaluated.

In certain embodiments, a step of comparing the propagated ultrasonic wave to the detected ultrasonic wave involves detecting and measuring energy loss and phase shifts between the propagated ultrasonic wave and the detected ultrasonic wave, and the step of evaluating the existence and extent of damage in the wire in the vicinity of the crimp connection involves correlating the measured energy loss and/or measured phase shift to an associated type and extent of damage.

It has been found that when an ultrasonic wave is propagated along a predetermined length of a wire in the immediate vicinity of a crimped connector, the wave energy is altered as it propagates through a damaged section of the wire (e.g., a broken, bent or nicked section). In those cases where the break is incomplete (e.g., a nick or notch), the phase of the wave is shifted. A break in one of the strands causes a substantial decrease in amplitude and energy of the wave. The magnitude of the changes depends on the magnitude of the defect, the number of affected strands in the wire, the strand gauge, and the total number of strands.

The parameters affecting measurements of the ultrasonic wave energy and phase shift include the wave frequency, wave mode, and initial amplitude, all of which may be optimized to facilitate detection and quantitative evaluation of defects at a crimped connector, including nicks, breaks and bends.

DETAILED DESCRIPTION OF THE INVENTION

Figure 1:
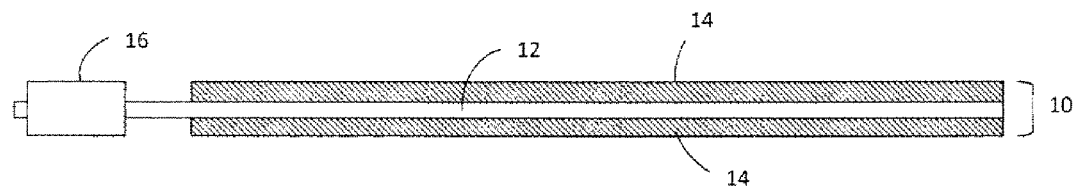
FIG. 1 is a schematic cross sectional view of a section of a wire in the immediate vicinity of a crimp connector.

Shown in FIG. 1 is a schematic representation of a terminal section of an insulated electrical conductor 10 comprising a wire 12 coated with an insulator 14, and having one or more crimped connectors 16. The wire may comprise multiple strands of wire. Crimped connectors are well known in the art and are described in the literature, such as in U.S. Pat. No. 7,181,942, which is hereby incorporated by reference in its entirety.

Figure 2A:
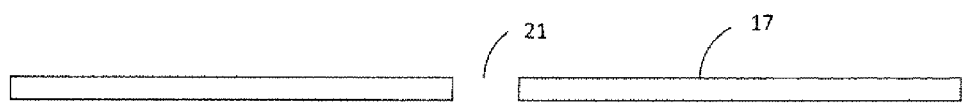
FIG. 2A is a schematic representation of a break in a wire strand.
Figure 2B:
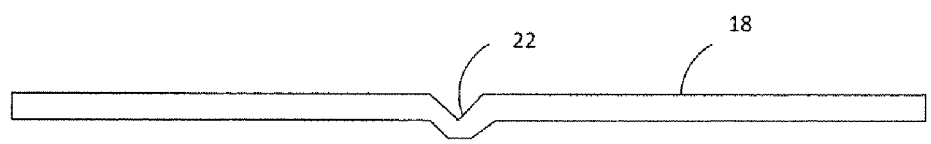
FIG. 2B is a schematic representation of a bend in a wire strand.
Figure 2C:
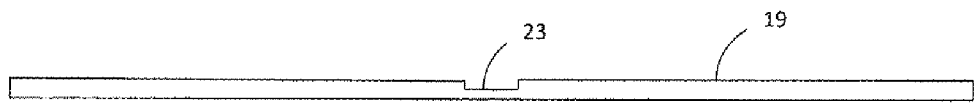
FIG. 2C is a schematic representation of a nick in a wire strand.

During the process of terminating a wire with a crimped connector, it is not unusual that defects are created in the conducting core or individual strands of a wire. The types of pathologies or defects that can be created in the individual strands of a wire during a process for terminating the wire with a crimped connector are represented schematically in FIGS. 2A, 2B, and 2C, which show a break 21, bend 22, and nick 23 in wire strands 17, 18 and 19, respectively.

Figure 3:
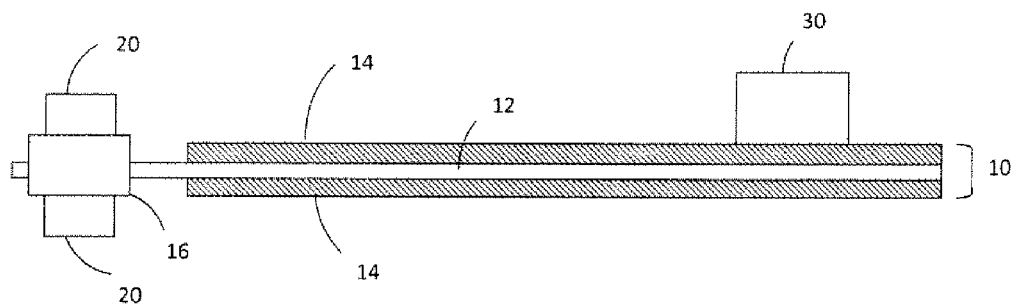
FIG. 3 is a schematic representation of an apparatus for detecting wire defects near a crimped connector.

FIG. 3 schematically illustrates an apparatus for detecting wire pathologies or defects near a crimp connector. The apparatus comprises transmitting transducers 20 for launching an ultrasonic wave mode into the wire (e.g., in a direction transverse to the longitudinal direction of the wire), causing a conversion of some of the compressional wave energy into shear wave propagation along the length direction of the wire.

The apparatus also includes a receiving transducer 30 that detects the ultrasonic wave and converts it into an electrical output for measurement and analysis. The electrical output from the receiving transducer is compared to either the output from a substantially identical wire and crimped connector that is known to be of good quality or it is compared with the electrical input from the transmitting transducer. FIG. 3, as shown, depicts the receiving transducer 30 on the exterior of the insulation of the wire to detect the wave. However, in an alternative embodiment (not shown), the receiving transducer may be in direct electrical communication with the wire in order to permit interrogation of the wire between two crimp connectors.

As described in U.S. Pat. No. 7,181,942, the ultrasonic wave transmitted into the wire can be launched at the same time and/or by an ultrasonically equipped device used for crimping the wire to a ferrule. For example, a crimped connector 16 can be installed using a RayChem model AP 1377 (M22520/37/01) crimper equipped with an ultrasonic transducer, which launches a shear wave that passes perpendicularly to the wire and the particle displacement is along the wave axis. This causes a longitudinal wave to be launched down the wire axis (i.e., longitudinally). However, this is not a limitation, as there are other means for launching ultrasonic wave modes into the wire.

As an ultrasonic wave mode travels along the wire it encounters energy loss mechanisms and/or phase shifts at defect or pathology locations. As the specific ultrasonic wave mode, which is affected by any existing defects or pathologies, passes through the length of wire, the resulting electrical waveform that is detected can be recorded, digitized and/or stored. The waveform may be compared with a waveform from a high quality crimped connector to determine whether the crimped connector is acceptable. Alternatively, or additionally, the system may be designed to make comparisons based on phase shifts and/or attenuation effects encountered in both absolute measurements and in comparison measurements.

A capacitive detector designed to differentiate between longitudinal and shear particle displacements may be installed at a predetermined longitudinal distance from the location at which the compressional wave is launched into the wire. As the shear wave, which is affected by any existing pathologies, passes through the length of wire between the transmitter and the detector (ultrasonic wave receiver), the resulting electrical waveform record can be digitized and stored, such as for analysis by a computer algorithm.

It should be understood that the illustrated positions of the ultrasonic transmitter and ultrasonic receiver can be reversed, provided that the ultrasonic wave transmitting transducer is positioned in reasonable proximity to the crimped wire connector (i.e., adjacent the crimped wire connector to facilitate launching of the ultrasonic wave into the crimped wire), and the ultrasonic wave receiving transducer is positioned a predetermined distance from the transmitting transducer such that an ultrasonic wave launched into the wire and propagated along the length direction of the wire will pass through the crimped wire connector before being received at the receiving transducer.

Physical embodiments include but are not limited to different transducers, different mountings, and different couplings.

In the case of an incomplete break (e.g., a nick) the wave is changed. When a wave propagated through a nicked strand is combined with waves propagated through undamaged strands, the phase is shifted. Upon reception, the electrical output from the receiving transducer is phase-compared with the electrical input to the transmitting transducer in, for example, a pulsed phase-locked loop arrangement. The phase shift is indicative of a bend and/or nick pathology or damage. While a nick or bend in a wire strand will result in phase shift, a break in a wire strand will cause a further decrease in amplitude, and hence a further decrease in wave energy. In all cases, the magnitude of the change (phase shift or energy loss) will depend on the size of the defect, the number of affected strands, the strand gauge, and the total number of strands.

In the case of insufficient coupling between the terminal of the wire (pigtail) an insufficient signal will be detected. In all cases the frequency dependence of the detected wave also depends upon the transducer mode. Shape and size of the transducer, and the contact asperity pattern.

Comparisons may be made by a person using an oscilloscope or can be done by a computer algorithm operating on the digitized information.

Figure 4:
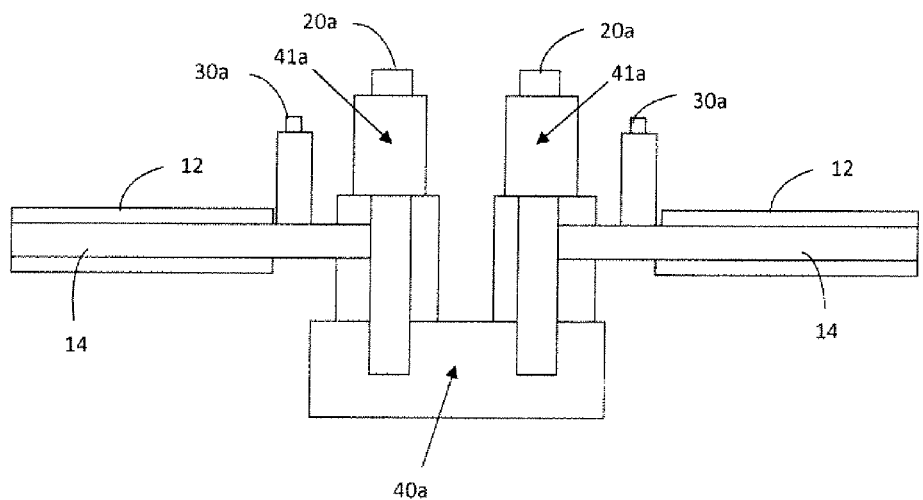
FIG. 4 is a schematic representation of a cross sectional view of a terminal block with wires connected.
Figure 5:
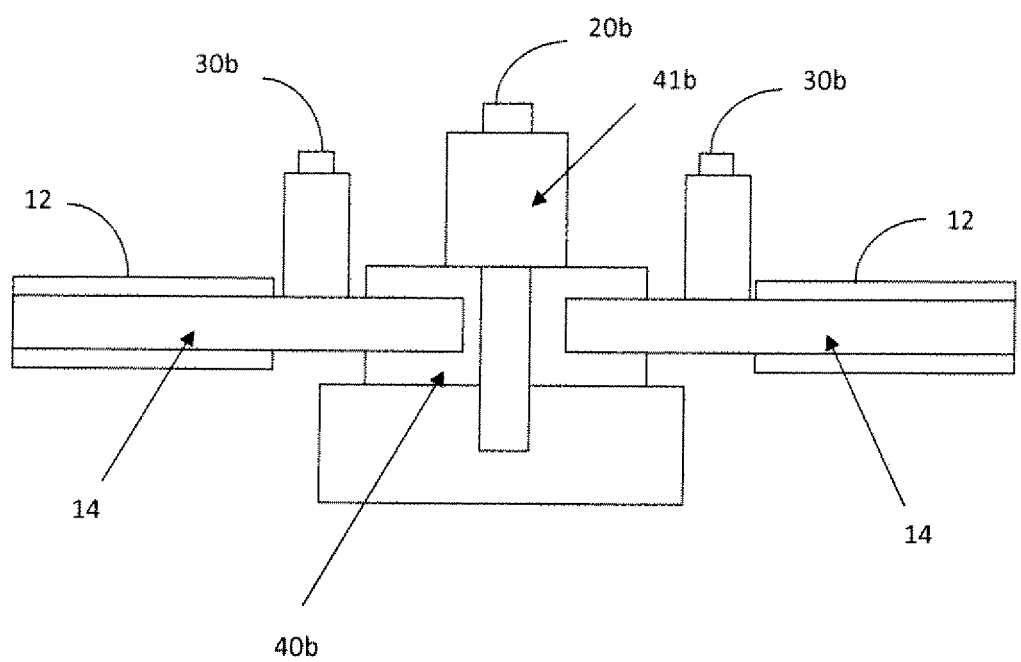
FIG. 5 is a schematic representation of a cross sectional view of an alternate terminal block with wires connected.

In another embodiment, this technology is applied to wires that are spliced through a compression mechanism on a terminal block 40a, 40b (FIGS. 4 and 5). Transducers 20a, 20b emit an ultrasonic wave which travels through the connecting mechanism 41a, 41b of the terminal block. An ultrasonic mode passes along the wire 14 and is detected with transducer 30a, 30b selected to receive the wave mode in the wire. The amplitude of the wave mode of the received wave depends upon asperity contact density and contact pattern between the terminal block 40a, 40b and the wire 14. This embodiment allows for determination of a properly tensioned terminal block so that minimum resistance across the connector is achieved and maintained. The technique can be employed during service life to assure no slippage or oxidation/corrosion at the junction between wire and block.

While preferred embodiments and example configurations of the invention have been herein illustrated, shown and described, it is to be appreciated that various changes, rearrangements and modifications may be made therein, without departing from the scope of the invention as defined by the appended claims. It is intended that the specific embodiments and configurations disclosed are illustrative of the preferred and best modes for practicing the invention, and should not be interpreted as limitations on the scope of the invention as defined by the appended claims and it is to be appreciated that various changes, rearrangements and modifications may be made therein, without departing from the scope of the invention as defined by the appended claims.

What is claimed is:

1. A process for evaluating and quantifying damage associated with a crimped wire connector comprising:
   launching a launched ultrasonic wave into a wire with an ultrasonic transmitting transducer that is in a vicinity of the crimped connector at a launch location, the wire having a length direction;
   detecting a resulting ultrasonic wave propagated along the length direction of the wire with an ultrasonic receiving transducer at a receiving location that is offset from the crimped connector along the length direction of the wire and a predetermined distance away from the launch location in the length direction;
   comparing the resulting ultrasonic wave with a known ultrasonic waveform for the crimped wire connector.

2. The process of claim 1, the step of detecting further comprising:
   digitizing and storing the resulting ultrasonic wave.

3. The process of claim 2, the process further comprising:
   determining if a pathology exists on the wire.

4. The process of claim 3, wherein the pathology is a break, a bend or a nick in the wire.

5. The process of claim 4, wherein the ultrasonic transmitting transducer and the ultrasonic receiving transducer are mounted on a crimp tool.

6. The process of claim 1, where the vicinity comprises adjacent.

7. The process of claim 1, where in the vicinity comprises substantially adjacent.

8. A process for detecting a defect in a crimped wire connector comprising:
   launching a launched ultrasonic wave into a wire with an ultrasonic transmitting transducer that is substantially adjacent to the crimped connector at a launch location, the wire having a length direction;
   detecting a resulting ultrasonic wave propagated along the length direction of the wire with an ultrasonic receiving transducer at a receiving location that is offset from the crimped connector along the length direction of the wire and a predetermined distance away from the launch location in the length direction;
   digitizing and storing the resulting ultrasonic wave;
   comparing the resulting ultrasonic wave with a known ultrasonic waveform for the crimped wire connector.

9. The process of claim 8, the process further comprising: determining if a defect exists on the wire.

10. The process of claim 9, wherein the defect is a break, a bend or a nick in the wire.

11. The process of claim 8, wherein the ultrasonic transmitting transducer is mounted on a crimp tool.

12. The process of claim 8, wherein the ultrasonic receiving transducer is mounted on a crimp tool.

13. An apparatus for evaluating and quantifying damage associated with a crimped wire connector comprising:
   a wire having a crimped wire connector, the wire having a length direction;
   an ultrasonic wave transmitting transducer positioned adjacent the crimped wire connector to facilitate launching of an ultrasonic wave into the crimped wire; and
   an ultrasonic wave receiving transducer positioned offset from the crimped connector along the length direction of the wire and a predetermined distance from the transmitting transducer, such that an ultrasonic wave launched into the wire will pass through the crimped wire connector before being received at the receiving transducer, the predetermined distance being along the length direction of the wire.

14. The apparatus of claim 13, wherein the ultrasonic transmitting transducer is mounted on a crimp tool.

15. The apparatus of claim 14, wherein the ultrasonic receiving transducer is mounted on a crimp tool.

16. The apparatus of claim 15, further comprising a computer in electrical communication with the receiving transducer, where the computer is configured to:
   receive an electrical waveform corresponding to the resulting ultrasonic wave from the receiving transducer; and
   digitize and store the electrical waveform corresponding to the resulting ultrasonic wave from the receiving transducer.

* * * * *